(12) United States Patent
Nakakado

(10) Patent No.: US 9,308,132 B2
(45) Date of Patent: Apr. 12, 2016

(54) METHOD AND DEVICE FOR MANUFACTURING COMPOSITE SHEET

(71) Applicant: Masaki Nakakado, Osaka (JP)

(72) Inventor: Masaki Nakakado, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 14/416,765

(22) PCT Filed: Jul. 25, 2013

(86) PCT No.: PCT/JP2013/070179
§ 371 (c)(1),
(2) Date: Jan. 23, 2015

(87) PCT Pub. No.: WO2014/021189
PCT Pub. Date: Feb. 6, 2014

(65) Prior Publication Data
US 2015/0182386 A1 Jul. 2, 2015

(30) Foreign Application Priority Data
Aug. 2, 2012 (JP) .................................. 2012-171743

(51) Int. Cl.
*B32B 37/00* (2006.01)
*A61F 13/15* (2006.01)
(Continued)

(52) U.S. Cl.
CPC ..... *A61F 13/15634* (2013.01); *A61F 13/15658* (2013.01); *A61F 13/15699* (2013.01); *A61F 13/15707* (2013.01); *A61F 13/15731* (2013.01); *A61F 13/15804* (2013.01); *A61F 13/5323* (2013.01); *B32B 37/0046* (2013.01); *B32B 37/0053* (2013.01); *B32B 37/0076* (2013.01);
(Continued)

(58) Field of Classification Search
CPC ...... B32B 37/00; B32B 37/025; B32B 38/10; B41M 5/38207; B44C 1/17
See application file for complete search history.

(56) References Cited

U.S. PATENT DOCUMENTS

| | | | | |
|---|---|---|---|---|
| 5,925,439 A | * | 7/1999 | Haubach | A61F 13/5323 428/178 |
| 2006/0021695 A1 | * | 2/2006 | Blessing | A61F 13/15658 156/196 |
| 2010/0209664 A1 | * | 8/2010 | Sato | A61F 13/511 428/138 |

FOREIGN PATENT DOCUMENTS

| | | |
|---|---|---|
| JP | 2006-341455 A | 12/2006 |
| JP | 2007-130818 A | 5/2007 |

(Continued)

OTHER PUBLICATIONS

International Search report for corresponding International Application No. PCT/JP2013/070179 mailed Oct. 15, 2013.

*Primary Examiner* — Michael N Orlando
*Assistant Examiner* — Matthew Hoover
(74) *Attorney, Agent, or Firm* — Renner, Otto, Boisselle & Sklar, LLP

(57) ABSTRACT

A method including: a step of forming depressions and protrusions on a first continuous sheet between a first roll and a second roll; a placement step of placing a plurality of granular particles in depressed portions of the depressions and protrusions of the first continuous sheet; a step of laying a second continuous sheet on the first continuous sheet, thereby forming a sandwich structure; and a step of bonding the two sheets with each other along protruding portions of the depressions and protrusions of the first continuous sheet, wherein a circumferential velocity of the second roll is greater than a circumferential velocity of the first roll.

11 Claims, 8 Drawing Sheets

(51) Int. Cl.
*A61F 13/532* (2006.01)
*B32B 38/06* (2006.01)
*B32B 37/06* (2006.01)
*B32B 37/20* (2006.01)
*B32B 38/00* (2006.01)
*A61F 13/53* (2006.01)

(52) U.S. Cl.
CPC .................. *B32B 37/06* (2013.01); *B32B 37/20* (2013.01); *B32B 38/0012* (2013.01); *B32B 38/06* (2013.01); *A61F 2013/15821* (2013.01); *A61F 2013/15869* (2013.01); *A61F 2013/530481* (2013.01); *B32B 2555/02* (2013.01); *Y10T 156/1007* (2015.01)

(56) References Cited

FOREIGN PATENT DOCUMENTS

| | | | |
|---|---|---|---|
| JP | 2008-508052 | A | 3/2008 |
| JP | 2009-126107 | A | 6/2009 |
| JP | 2009-154424 | A | 7/2009 |
| JP | 2009-155741 | A | 7/2009 |
| JP | 2009-202506 | A | 9/2009 |

* cited by examiner

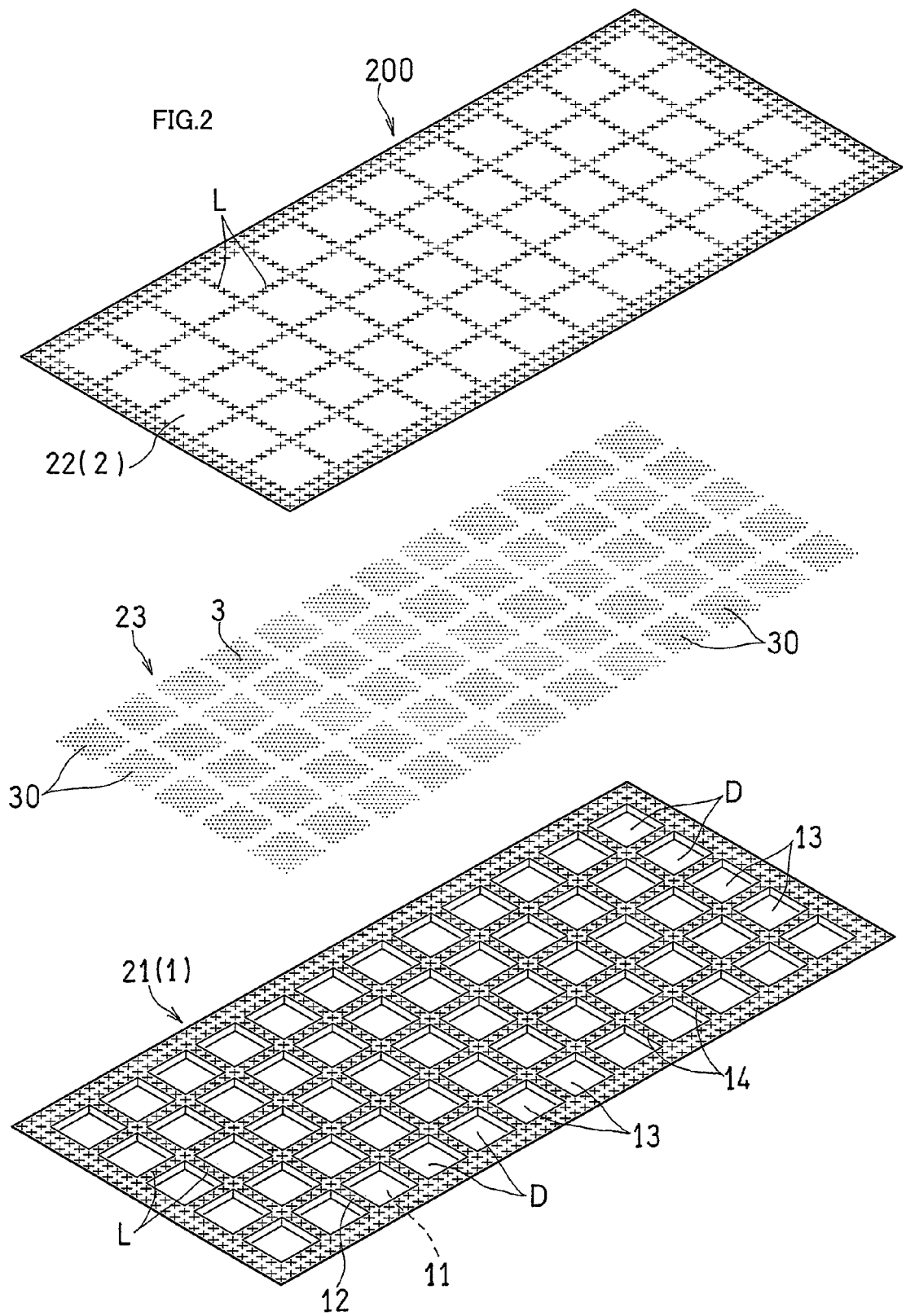

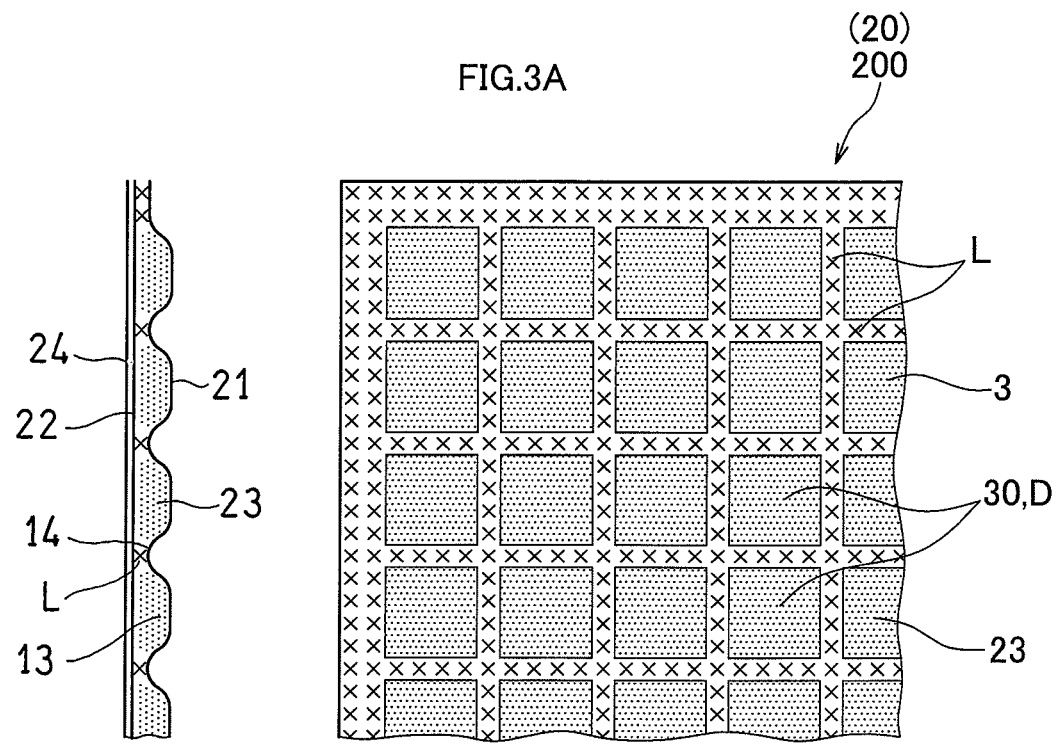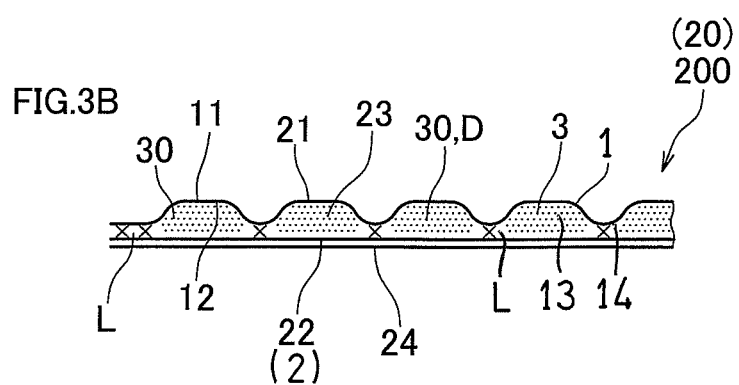

METHOD AND DEVICE FOR MANUFACTURING COMPOSITE SHEET

TECHNICAL FIELD

The present invention relates to a method and a device for manufacturing a composite sheet in which aggregate groups of granular particles are placed between a pair of air-permeable sheets.

BACKGROUND ART

Disposable worn articles such as disposable diapers or pants or sanitary products for women include an absorbent body capable of absorbing a bodily fluid. Such an absorbent body has a sandwich structure in which an absorbent core is sandwiched between two webs.

Recently, it has been proposed in the art to use an absorbent polymer made of granular particles as a main component of an absorbent core. In such a case, typically, a large number of aggregate groups of granular particles are placed separately from one another in the longitudinal direction and the width direction, and two webs are sealed (bonded) together along portions between the aggregate groups, thereby maintaining the placement pattern of the aggregate groups.

Two patent documents identified below are known to be related to such a technique.

CITATION LIST

Patent Literature

[First Patent Document] JP2008-508052W
[Second Patent Document] JP2007-130818A

SUMMARY OF INVENTION

In the manufacturing method of the first patent document, a carrier material is held in a predetermined pattern on a drum, and a suction force is made to act on the carrier material from inside the drum, thereby forming depressions in the carrier material, allowing granular particles to be placed in the depressions. With this method, however, depressions are formed in the carrier material by a suction force, and the volume of depressions for accommodating the granular particles is likely to be insufficient.

On the other hand, in the manufacturing method of the second patent document, a sheet is supplied to a meshing portion between a pair of rolls having protrusions and depressions to mesh with each other so as to give a protruding/depressed shape to the sheet, and granular particles are placed in the depressed portions in the sheet. With this conventional technique, however, forming depressed portions of a sufficient volume will give an excessive force acting upon the sheet, and the depressions and protrusions of the pair of rolls mesh with each other strongly, and the sheet will likely be damaged during production.

It is therefore an object of the present invention to provide a method and a device for manufacturing a composite sheet, by which depressed portions of a sufficient volume can be formed in the sheet without damaging the sheet.

A method of the present invention is a method for manufacturing a composite sheet in which a plurality of granular particles are placed in a predetermined pattern between two sheets, wherein the method uses a first roll having a plurality of first depressions and protrusions on a circumferential surface thereof, and a second roll having a plurality of second depressions and protrusions on a circumferential surface thereof, the second depressions and protrusions fitting (meshing) with the first depressions and protrusions, the method including:

a step of carrying a first continuous sheet along a plurality of protruding portions of the second depressions and protrusions of the second roll so as to supply the first continuous sheet into between the first roll and the second roll;

a step of causing some of the second depressions and protrusions of the second roll and some of the first depressions and protrusions of the first roll to rotate while fitting with each other, with the first continuous sheet interposed therebetween, thereby forming third depressions and protrusions on the first continuous sheet;

a placement step of placing a plurality of granular particles in depressed portions of the third depressions and protrusions;

a step of laying a second continuous sheet on the first continuous sheet so as to cover openings of the depressed portions of the third depressions and protrusions and the granular particles, thereby forming a sandwich structure; and a bonding step of bonding the two sheets together along the protruding portions of the third depressions and protrusions, wherein a circumferential velocity V2 of the second roll is greater than a circumferential velocity V1 of the first roll.

On the other hand, a device of the present invention is a device for manufacturing a composite sheet, in which a plurality of granular particles are placed in a predetermined pattern between two sheets, a first roll having a plurality of first depressions and protrusions on a circumferential surface thereof;

a second roll having a plurality of second depressions and protrusions on a circumferential surface thereof, the second depressions and protrusions fitting (meshing) with the first depressions and protrusions, carrying a first continuous sheet along a plurality of protruding portions of the second depressions and protrusions so as to supply the first continuous sheet into between the first roll and the second roll, wherein the first depressions and protrusions and the second depressions and protrusions rotate while meshing with each other with the first continuous sheet interposed therebetween, thereby forming a plurality of third depressions and protrusions on the first continuous sheet;

a placement device for placing a plurality of granular particles in depressed portions of the third depressions and protrusions;

an introduction roller for laying a second continuous sheet on the first continuous sheet so as to cover openings of the depressed portions of the third depressions and protrusions and the granular particles by the second continuous sheet, thereby forming a sandwich structure;

a bonding device for bonding the two sheets together along the protruding portions of the third depressions and protrusions; and a control device for rotating the rolls so that a circumferential velocity V2 of the second roll is greater than a circumferential velocity V1 of the first roll.

According to the present invention, the first continuous sheet to be shaped to have depressed portions for accommodating a plurality of granular particles is supplied to the introduction point between the first roll and the second roll by the second roll having the circumferential velocity V2 greater than the circumferential velocity V1 of the first roll.

The circumferential velocity V2 of the second roll is greater than the circumferential velocity V1 of the first roll, and the first continuous sheet is overfed at the introduction point. Therefore, even if depressions and protrusions are formed on the flat first continuous sheet between the first roll and the second roll, the sheet is not damaged, thus allowing large depressed portions to be formed on the first continuous sheet.

Moreover, the first continuous sheet is supplied to the introduction point along the second roll, i.e., while being wound around the second roll under tension. Therefore, even if the first continuous sheet is overfed, the sheet is unlikely to be excessively slackened at the introduction point, and the product will unlikely be wrinkled or creased.

BRIEF DESCRIPTION OF DRAWINGS

FIG. 2 is an exploded perspective view of an absorbent body of the worn article as seen from the non-skin-contact surface side.

FIG. 3A is a plan view of the absorbent body, FIG. 3B is a width-wise cross-sectional view thereof, and FIG. 3C is a longitudinal cross-sectional view thereof.

DESCRIPTION OF EMBODIMENTS

Figure 1:
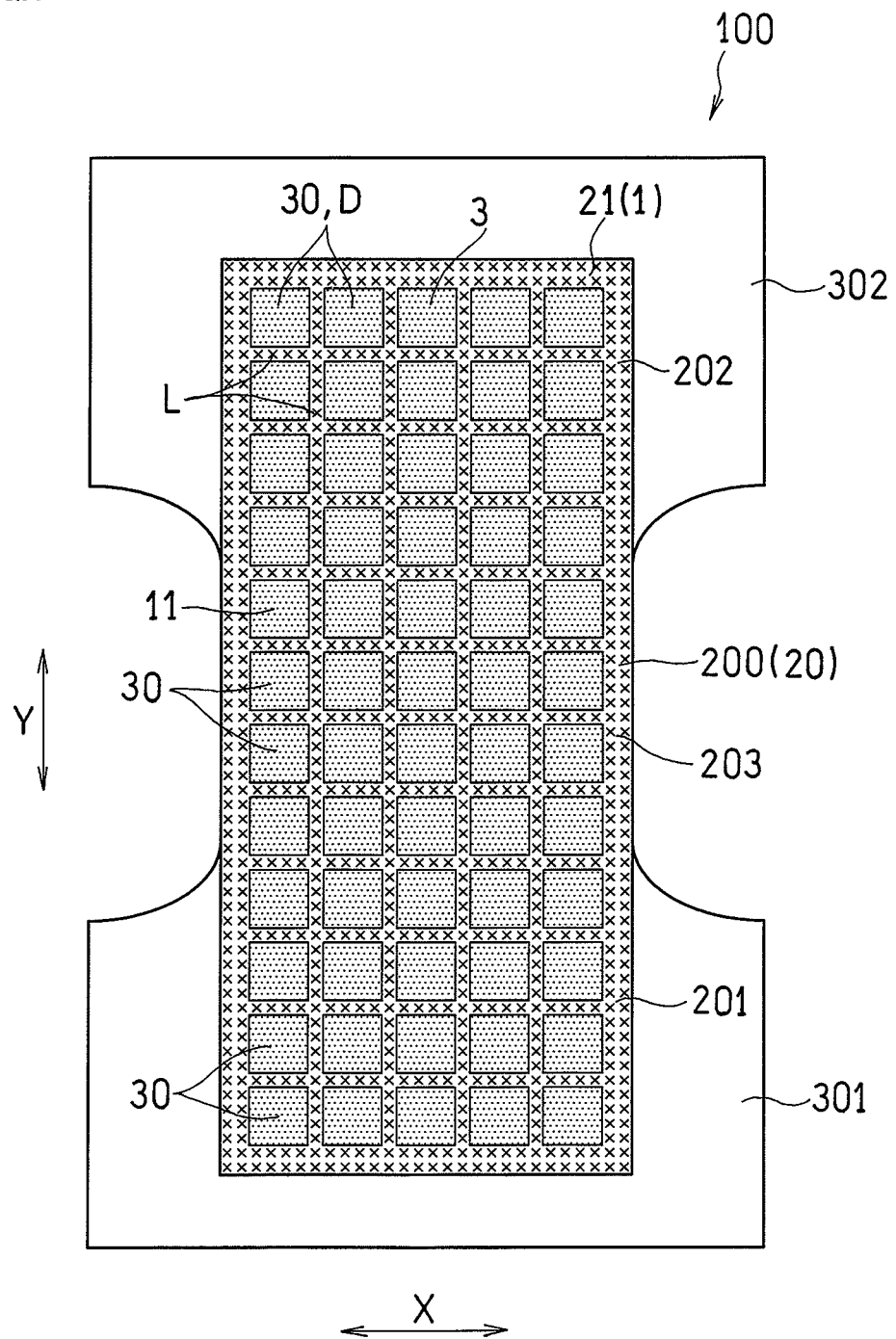
FIG. 1 is a plan view of a worn article according to an embodiment of the present invention.

Preferably, a pitch P2 of the second depressions and protrusions is greater than a pitch P1 of the first depressions and protrusions. Specifically, it is set so that V2/P2=V1/P1 holds.

Thus, even if the circumferential velocities of the two rolls are different from each other, the depressions and protrusions of the two rolls can fit with each other.

Preferably, the first and second rolls are separately rotated with no rotational force being transferred therebetween via the first and second depressions and protrusions.

Thus, since the two rolls do not transfer a rotational force via the depressions and protrusions, it is possible to prevent the first continuous sheet from being strongly pinched and damaged between the protruding portions of the rolls.

More preferably, the first continuous sheet is air-permeable; and in the placement step, the method further includes a step of causing a suction force to act on the depressed portions of the first continuous sheet from the depressed portions of the first depressions and protrusions of the first roll, thereby holding the first continuous sheet on the circumferential surface of the first roll while holding the granular particles in the depressed portions of the third depressions and protrusions through the first continuous sheet.

In such a case, the air suction force not only holds the granular particles on the depressed portions of the first continuous sheet, but the air suction force also draws the depressed portions of the first continuous sheet onto the depressed portions of the first roll. This may ensure the shaping process of the sheet, and allow the depressed portions of the sheet to be formed deeper in the shaping process.

More preferably, the first continuous sheet has a greater stretchability in a width direction, perpendicular to a carrying direction, than that in the carrying direction.

In the device of the present invention, the depressions and protrusions of the first continuous sheet are formed at least in the circumferential direction of the first roll, but depressions and protrusions may further be formed in the axial direction of the roll. In such a case, if the first continuous sheet has a greater stretchability (extensibility) in the width direction, the first continuous sheet is less likely to be damaged during the shaping of the depressions and protrusions.

More preferably, the sheets contain a thermoplastic resin; and the bonding step includes ultrasonically welding and thereby bonding the sheets with each other (the sheets are bonded with each other by ultrasonic welding in the bonding step).

If large depressed portions are formed on the first continuous sheet as in the present invention, it increases the reliability that a large number of granular particles can be accommodated in the depressed portions, thereby preventing the granular particles from remaining between the ultrasonic horn and the protruding portions to inhibit the ultrasonic welding.

EMBODIMENTS

The present invention will be understood more clearly from the description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

One embodiment of the present invention will now be described with reference to the drawings.

Worn Article 100:

As shown in FIG. 1, the worn article 100 of the present embodiment includes an absorbent body (diaper body) 200, a front around-torso member 301, and a back around-torso member 302. The absorbent body 200 includes a front portion 201 covering a front torso of the wearer, a back portion 202 covering the back torso of the wearer, and a crotch portion 203 covering the crotch between the front portion 201 and the back portion 202.

The crotch portion 203 is continuous with the front portion 201 and the back portion 202, and extends in the longitudinal direction (carrying direction) Y perpendicular to the girth direction (width direction) X. The front around-torso member 301 and the back around-torso member 302 may be bonded together when worn, or may be pre-bonded before being worn.

The absorbent body 200 may be provided with three-dimensional gathers (not shown).

The absorbent body 200 may include around-leg portions narrowed in conformity with the legs of the wearer.

Moreover, portions of the absorbent body 200 to be the around-leg portions may be provided with elastic members for fitting the worn article 100 to the wearer. The elastic members may be, for example, a plurality of rubber threads, rubber tapes, a film, a material including a thermoplastic resin, or the like. These materials may be provided in the front portion 201 and the back portion 202 as elastic members for fitting the worn article 100 to the wearer.

As shown in FIG. 2, the absorbent body 200 includes a top sheet 21 to be in contact with the skin surface of the wearer, a cover sheet 22 to be not in contact with the skin surface, and an absorbent core 23. The top sheet 21 and the cover sheet 22 of FIGS. 3B and 3C are welded together along lattice-shaped welded lines L, L extending in the length and width directions as shown in FIG. 3A, thereby forming a sandwich structure in which the core 23 is sandwiched therebetween. That is, as shown in FIG. 3A, the core 23 is surrounded by the top sheet 21 and the cover sheet 22 welded together along the welded lines L, L.

Note that the welded portions are denoted by 'xx' in different figures.

The top sheet 21 and the cover sheet 22 of FIG. 3B are formed by liquid-permeable and air-permeable non-woven fabric sheets. A non-liquid-permeable back sheet 24 is attached to the back surface of the cover sheet 22, and the absorbent body 200 is covered by the back sheet 24.

Note that the non-woven fabric sheet may be a thermoplastic resin non-woven fabric sheet such as polypropylene, polyethylene, polyester, or the like, and it may also be a non-woven fabric sheet obtained by blending together non-thermoplastic fibers such as cotton or rayon with the thermoplastic resin fibers.

The core 23 includes a large number of absorbent granular particles 3. The granular particles 3 are made of a well-known absorbent high-molecular polymer whose average granular diameter is typically about 10 μm to about 1,000 μm before absorbing moisture and which swell after absorbing moisture to a volume several times to several hundreds of times larger.

Note that the granular particles 3 are denoted by a larger number of minute dots in different figures.

The core 23 of FIG. 3A includes aggregate groups 30 placed in a large number of placement areas D, the aggregate groups 30 each having an aggregate of a large number of granular particles 3. The aggregate groups 30, 30 are separately arranged in the placement areas D, D partitioned by lattice-shaped welded lines L, L extending in the length and width directions. That is, the placement areas D, D, in which the aggregate groups 30, 30 are placed, are partitioned from one another by the welded lines L, L.

In other words, each aggregate group 30 is composed of an aggregate of a large number of granular particles 3, and the aggregate groups 30 are arranged in the length and width directions with welded lines L, L therebetween, as shown in FIG. 3A. As shown in FIG. 3A, a larger number (three or more) of aggregate groups are arranged in the length and width directions.

A welded line L does not need to be completely continuous, and may be an intermittent array of welded positions such that the granular particles 3 in one aggregate group 30 cannot easily move into other aggregate groups 30.

That is, the welded lines L, L may be formed to such a degree that it is possible to suppress the movement of granular particles 3 from one of the aggregate groups 30, arranged in a predetermined pattern, into another.

The arrangement of the aggregate groups 30 may be any predetermined pattern, and does not need to be a regular array extending in the length and width directions. The number (volume) of granular particles 3 contained in each aggregate group 30 does not need to be generally equal to that in other groups, and the number (volume) of each group 30 may be determined based on the amount of bodily fluid to be discharged.

As shown in FIG. 3A, the aggregate groups 30 may be rectangular or circular, and the length of each side or the diameter thereof may be some millimeters to about 10 millimeters. The pitch at which the aggregate groups 30, 30 are placed may be about 10 mm to about ten-odd mm.

Next, a device for manufacturing the absorbent body 200 will be described with reference to FIGS. 4 to 8.

This device includes a second roll 6, a dispenser device 5, first and second introduction rollers 71 and 72, and an ultrasonic horn (an example of the bonding device) 81, around a first roll 4.

The first and second introduction rollers 71 and 72 are rollers for introducing a carrier web (first continuous sheet) 1 and a cover web (second continuous sheet) 2 onto the circumference of the second roll 6 and the first roll 4, respectively.

Figure 5:
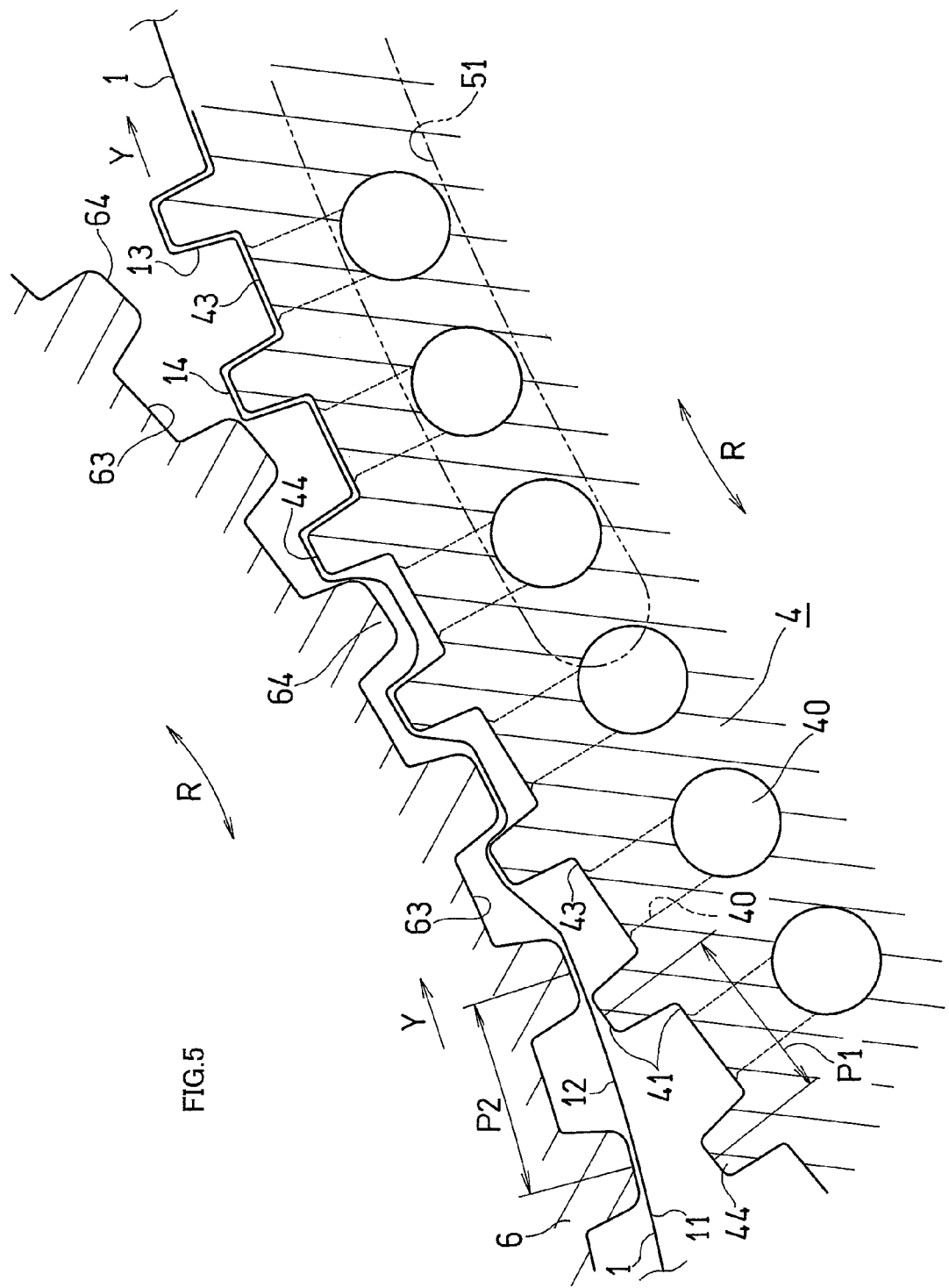
FIG. 5 is a cross-sectional view showing an introduction point at which depressions and protrusions of first and second rolls mesh with each other.

As shown in FIG. 5 on an enlarged scale, the first and second rolls 4 and 6 include first roll depressed and protruding portions 43 and 44 (first depressions and protrusions) and second roll depressed and protruding portions 63 and 64 (second depressions and protrusions) on the circumferential surfaces thereof.

The first roll depressed and protruding portions 43 and 44 and the second roll depressed and protruding portions 63 and 64 are formed with a predetermined regular first pitch P1 and a predetermined regular second pitch P2, respectively, and include a large number of depressed portions 43, 63 and a large number of protruding portions 44, 64 repeating in the circumferential direction R. The pitch P2 of the second roll depressed and protruding portions 63 and 64 is greater than the pitch P1 of the first roll depressed and protruding portions 43 and 44.

For the sake of measurement, the term "pitch (P1, P2)" is defined herein by the distance in the circumferential direction between centers of protruding portions, as shown in FIG. 5.

The first and second rolls 4 and 6 are separately rotated by a driving device (not shown), and no rotational force is transferred therebetween via the first roll depressed and protruding portions 43 and 44 and the second roll depressed and protruding portions 63 and 64. The driving device may include motors separately provided for the first and second rolls 4 and 6 and control devices for controlling the speed of the motors, or may include one motor and a control device for transferring the rotational force of this motor to the rolls via a timing belt and a pulley.

The control device rotates the rolls 4 and 6 so that the circumferential velocity V2 of the second roll is greater than the circumferential velocity V1 of the first roll. That is, the circumferential velocity may be set so that the following holds.

$$V2/P2 = V1/P1 \qquad (1)$$

Thus, the first roll depressed and protruding portions 43 and 44 and the second roll depressed and protruding portions 63 and 64 having different pitches from each other can smoothly fit with each other with no interference therebetween at the introduction point of the carrier web 1 between the first roll 4 and the second roll 6.

Now, the relationship of Expression 1 may not always need to be satisfied.

For example, as long as the amount of time for one rotation (cycle time) of the first roll 4 and that of the second roll 6 are each constant, the circumferential velocity V1 of the first roll 4 may temporarily become slightly greater than the circumferential velocity V2 of the second roll 6 during one rotation of the rolls 4 and 6.

That is, the relationship may be such that Expression 2 below is satisfied.

$$V2a/P2a = V1a/P1a \qquad (2)$$

(where $V2a$ is the average circumferential velocity for one rotation of the second roll 6;

$P2a$ is the average pitch of the second roll 6;

$V1a$ is the average circumferential velocity for one rotation of the first roll 4; and $P1a$ is the average pitch of the first roll 4)

Figure 4:
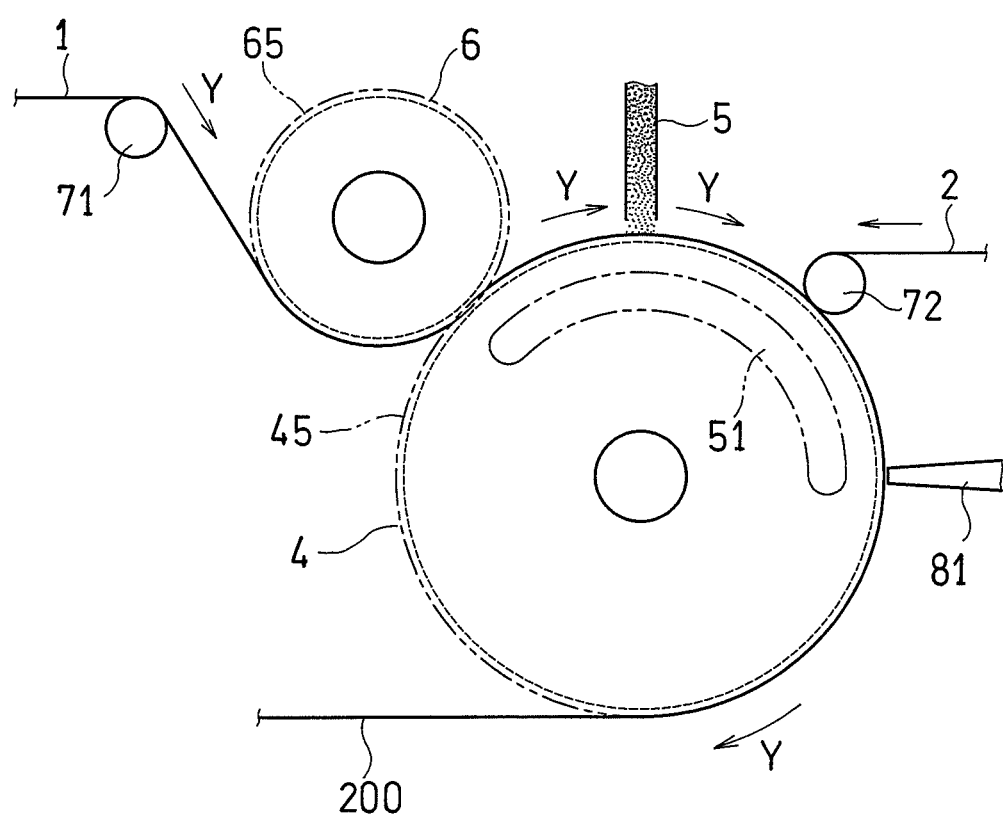
FIG. 4 is a layout diagram of a device for manufacturing the absorbent body.

As shown in FIGS. 4 and 5, the second roll 6 carries the carrier web 1 along the plurality of protruding portions 64 to supply the carrier web 1 into between the second roll 6 and the first roll 4.

As shown in FIG. 5, the first and second rolls 4 and 6 rotate while the first roll depressed and protruding portions 43 and 44 and the second roll depressed and protruding portions 63 and 64 fit with each other at the carrier web introduction point with the carrier web 1 being interposed therebetween, thereby forming a plurality of depressed portions 13 and a plurality of protruding portions 14 (the third depressions and protrusions) on the carrier web 1.

Note that the circumferential velocity V2 may be greater than the circumferential velocity V1 by about 1% to about 15%. Under 1%, there will be substantially no advantageous effect from overfeeding. On the other hand, over 15%, the carrier web 1 may likely be wrinkled or creased.

The length of the depressed portion 43 of the first roll 4 in the circumferential direction R is longer than the length of the protruding portion 64 of the second roll 6 in the circumferential direction R. On the other hand, the length of the protruding portion 44 of the first roll 4 in the circumferential direction R may be shorter than the length of the protruding portion 64 of the second roll 6 in the circumferential direction R. The protruding portions 44 and 64 of the first roll 4 and the second roll 6 having such dimensions will likely produce larger depressed portions 13 on the carrier web 1.

Moreover, even though the circumferential velocity V2 of the second roll 6 is greater than the circumferential velocity V1 of the first roll 4, the protruding portions 64 of the second roll 6 and the protruding portions 44 of the first roll 4 will not interfere with each other.

The depressed portions 43 of the first roll 4 may have suction holes 40. Each suction hole 40 is allowed, with predetermined timing, to communicate with a suction source (negative pressure source) (not shown) via an oblong hole 51 indicated by a two-dot-chain line.

The suction hole 40 causes a suction force to act upon the depressed portion 13 of the carrier web 1 via the depressed portion 43 of the first roll 4, thereby maintaining the carrier web 1 in a shape that conforms to the circumferential surface of the first roll 4.

As shown in FIG. 5, the first roll 4 carries the carrier web 1 along a predetermined carrying path while the first surface 11 of the air-permeable carrier web 1 is held by suction on the carrying surface 41 having a shape with depressions and protrusions. In the present embodiment, the first surface 11 forms the skin-contact surface to be in contact with the skin of the wearer.

Figure 6:
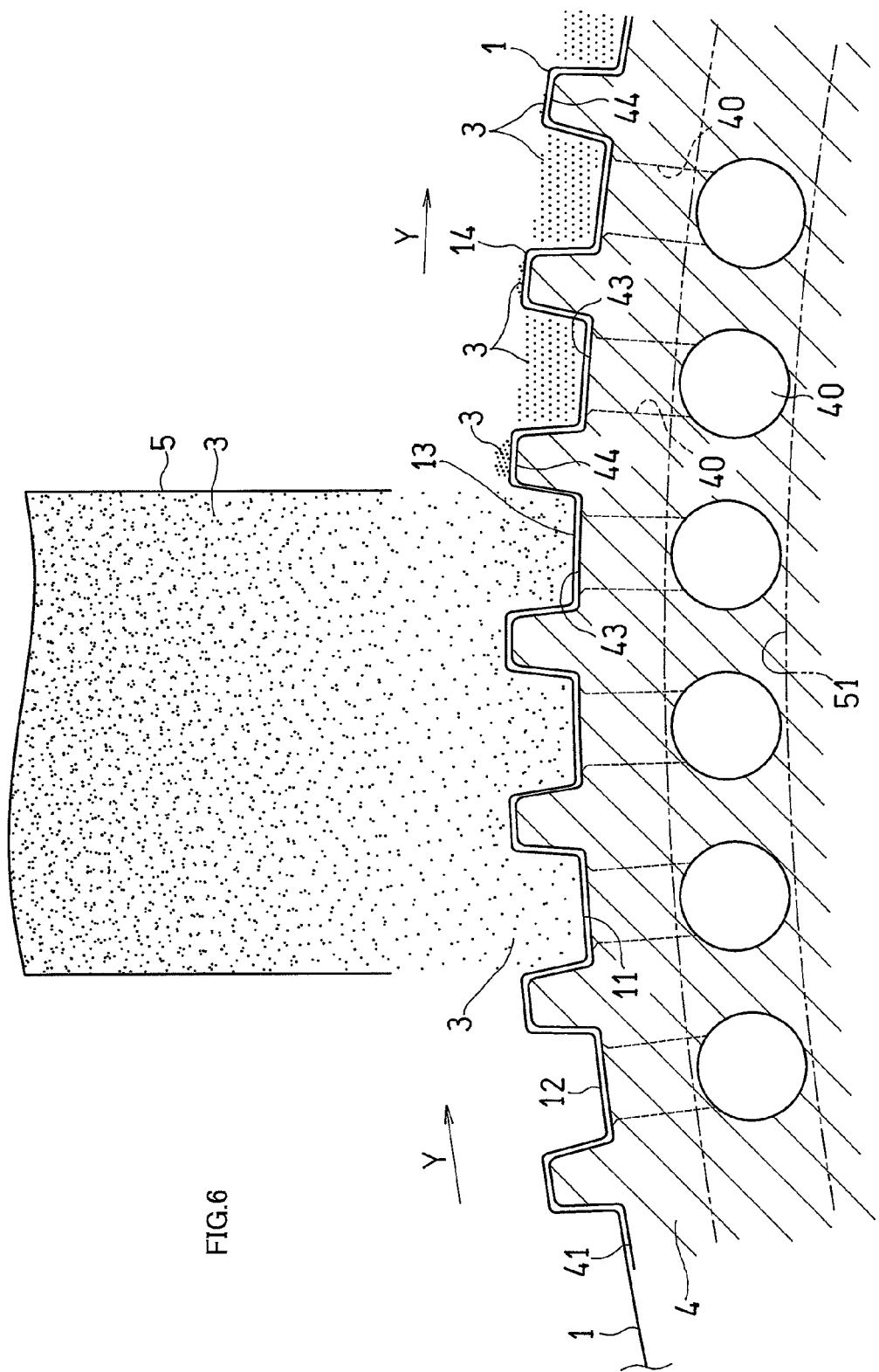
FIG. 6 is a cross-sectional view showing a dispensing point at which granular particles are dispensed.

The dispenser device 5 of FIG. 4 dispenses a countless (large) number of granular particles 3 onto the second surface 12, opposite to the first surface 11, of the carrier web 1 being carried, between the second introduction roller 72 and the second roll 6, i.e., at the dispensing point of FIG. 6. The granular particles 3 are dispensed intermittently or continuously so that a predetermined amount is dispensed per unit area of the carrier web 1.

As shown in FIG. 6, the suction holes 40 communicate with the suction source (not shown) via the oblong hole 51, and an air is drawn into the suction hole 40 through the carrier web 1. With the suction of an air, the granular particles 3 are held in the depressed portion 13 of the carrier web 1.

The suction holes 40 provided in a plate well known in the art are connected to the suction source (not shown) via the arc-shaped oblong hole 51 indicated by a two-dot-chain line of FIG. 4. The oblong hole 51 is provided so as to extend from the introduction point between the first roll 4 and the second roll 6 to the bonding point where bonding is done by the ultrasonic horn 81. In between, the granular particles 3 are held by suction within the depressed portions 13 of FIG. 6 via the carrier web 1.

The dispenser device 5 and the suction hole 40 form an example of the placement device of the present invention. Note that in order to remove the granular particles 3 on the protruding portions 14 of the carrier web 1, air-discharging holes may be provided on the surface of the protruding portions 44 of the first roll 4 so that the granular particles 3 are accommodated within the depressed portions 13 and are prevented from remaining on the protruding portions 14.

Figure 7:
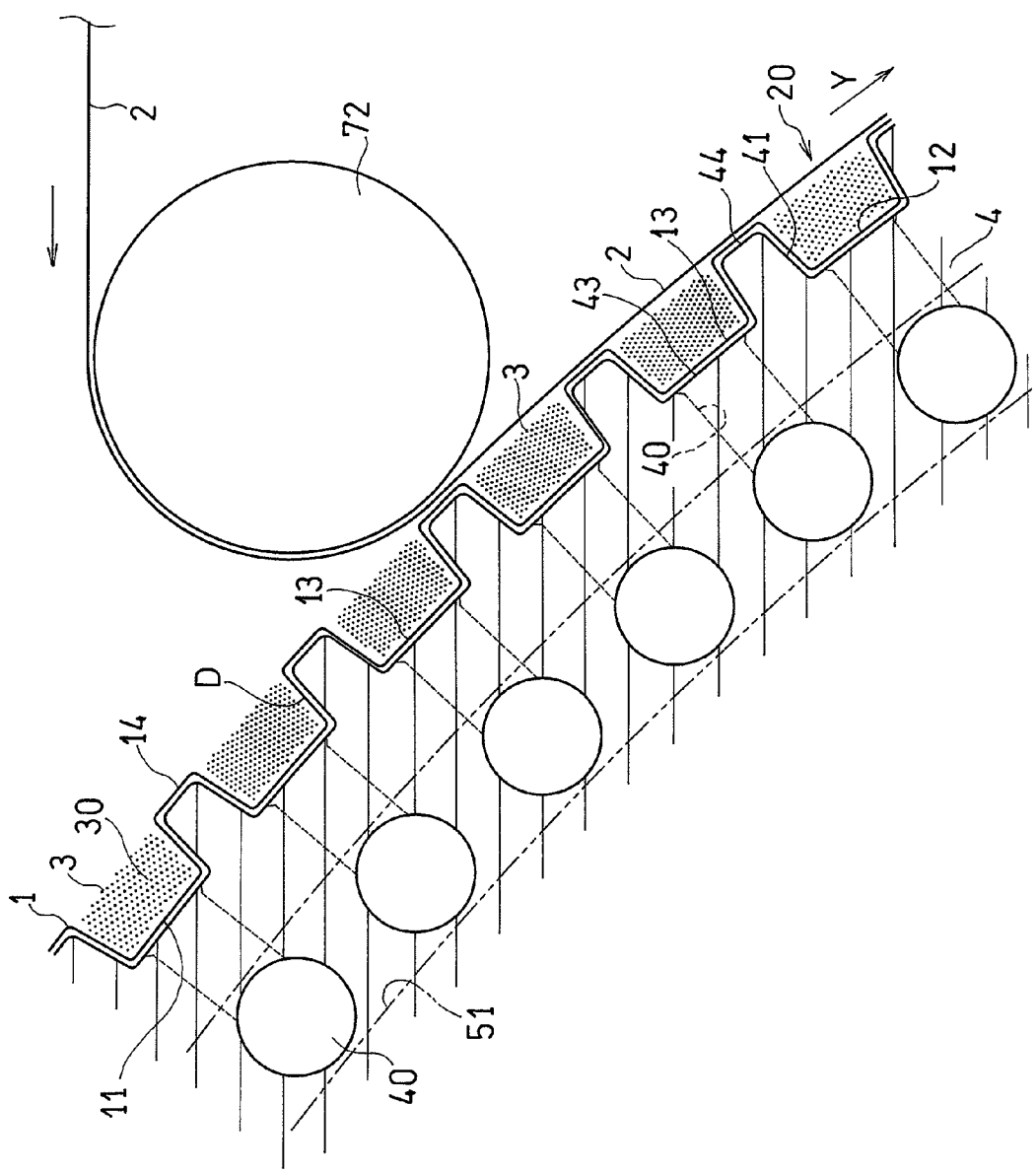
FIG. 7 is a cross-sectional view showing a position at which a second continuous sheet is introduced.

The second introduction roller 72 of FIG. 4 introduces the cover web 2 into the carrying path, downstream of the dispenser device 5 along the carrying path of the carrier web 1, so as to produce the sandwich structure 20 in which the second surface 12 of the carrier web 1 of FIG. 7 and the granular particles 3 are covered by the cover web 2. That is, the second introduction roller 72 lays the cover web 2 over the carrier web 1 so as to form the sandwich structure in which the openings of the depressed portions 13 of the carrier web 1 and the granular particles 3 are covered by the cover web 2.

Figure 8:
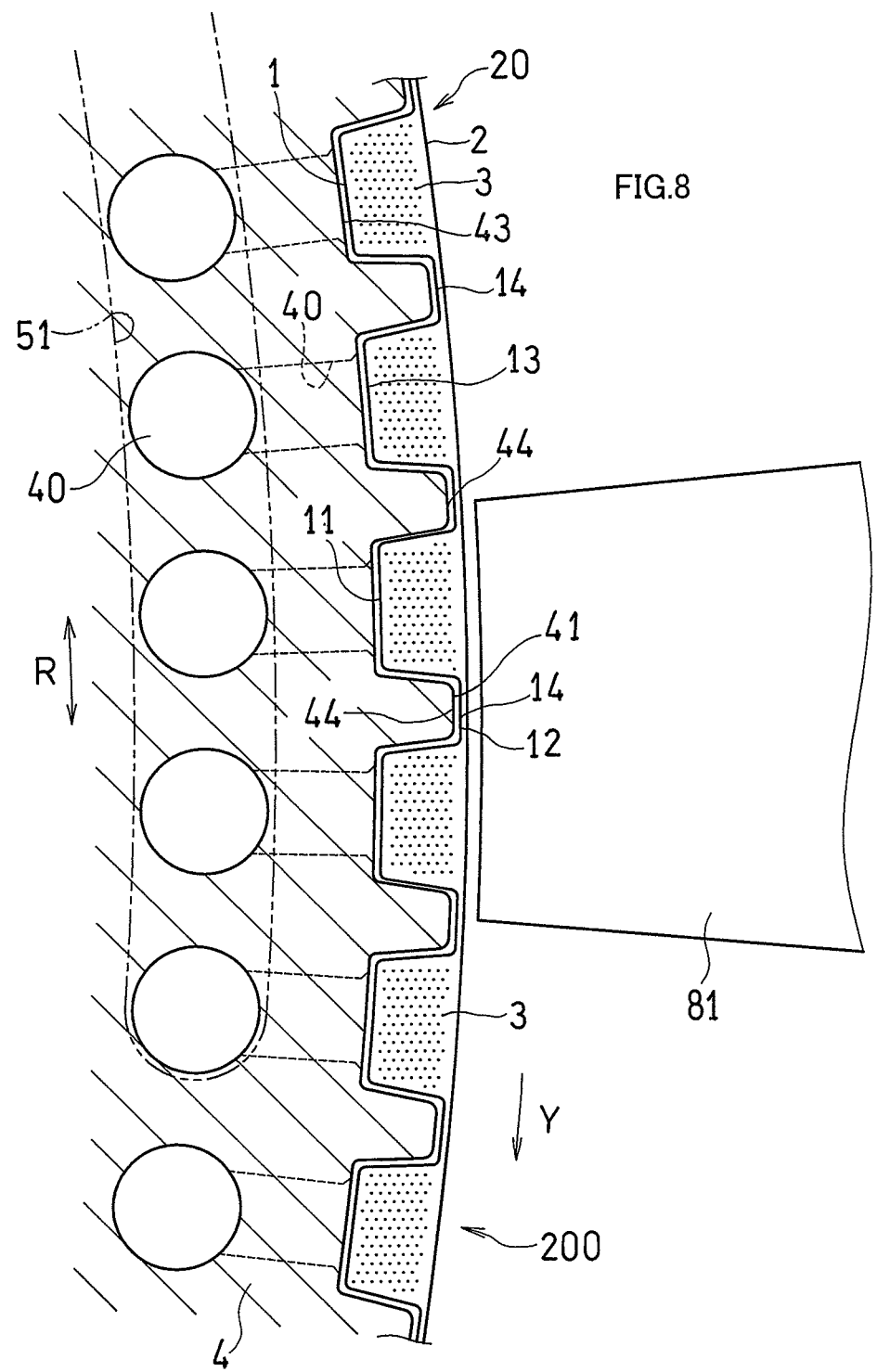
FIG. 8 is a cross-sectional view showing a position at which ultrasonic welding is performed.

The ultrasonic horn 81 (an example of the bonding device) of FIG. 4 gives the vibration energy to the webs 1 and 2 in cooperation with an anvil (the protruding portions 44) formed on the carrying surface 41 of the first roll 4 of FIG. 8, downstream of the second introduction roller 72 along the carrying path of the carrier web 1. Thus, the carrier web 1 and the cover web 2 are welded together on the surface of the protruding portions 44 of FIG. 8.

Note that with welding (sealing) using ultrasonic vibrations, mechanical vibrations are ultrasonically transmitted to the horn 81, so that the thermoplastic webs 1 and 2 pass through between the horn 81 and the anvil while being pressurized, thereby welding the webs with each other by frictional heat.

As described above, while the first roll 4 and the second roll 6 respectively include the depressed and protruding portions 43 and 44 and the depressed and protruding portions 63 and 64, continuous with each other in the circumferential direction R, these depressions and protrusions are provided also in the axial direction of the rolls 4 and 6. For the axial direction, the carrier web 1 cannot be overfed. Therefore, the carrier web 1 is preferably a web that easily stretches in the axial direction, i.e., the width direction X of FIG. 1.

For example, the carrier web 1 preferably has a greater stretchability in the width direction, perpendicular to the carrying direction, than that in the carrying direction.

Next, a method for manufacturing the absorbent body 200 will be described.

As shown in FIG. 4, the carrier web 1 is introduced onto the second roll 6 by the first introduction roller 71. The carrier web 1 having been introduced onto the second roll 6 is carried along the plurality of protruding portions 64 of the second roll 6 of FIG. 5 so as to be supplied to the introduction point between the first roll 4 and the second roll 6.

At the introduction point shown in FIG. 5, the rolls 4 and 6 rotate while some of the depressed and protruding portions 63 and 64 of the second roll 6 and some of the depressed and protruding portions 43 and 44 of the first roll 4 fit with each other with the carrier web 1 interposed therebetween. This starts forming the depressed portions 13 and the protruding portions 14 on the carrier web 1.

Now, the circumferential velocity V2 of the second roll 6 is greater than the circumferential velocity V1 of the first roll 4, and the carrier web 1, which is supplied while being wound around the second roll 6, is excessively supplied (overfed)

into the introduction point. Therefore, even if the depressed portions 13 and the protruding portions 14 are formed on the carrier web 1, the carrier web 1 is unlikely to be damaged.

On the other hand, while the circumferential velocities V2 and V1 of the rolls 6 and 4 are different from each other, the pitches P2 and P1 of the depressions and protrusions of the rolls 6 and 4 are set according to the circumferential velocities V2 and V1. Therefore, the rolls 6 and 4 can continue to rotate.

The first and second rolls 4 and 6 may be separately rotated with no rotational force being transferred therebetween via the first roll depressed and protruding portions 43 and 44 and the second roll depressed and protruding portions 63 and 64. In such a case, the carrier web 1 is less likely to be rubbed and damaged between the tooth flank of the protruding portion 44 of the first roll 4 and the tooth flank of the protruding portion 64 of the second roll 6.

Downstream of the introduction point, the suction hole 40 communicates with the oblong hole 51 so that the depressed portions 13 of the carrier web 1 are sucked onto the depressed portions 43 of the first roll 4. Therefore, the shape of the depressed portions 13 of the carrier web will become closer to the shape of the depressed portions 43 of the first roll.

On the other hand, the carrier web 1 includes depressions and protrusions not only in the circumferential direction R, but also in the axial direction, i.e., the width direction X (FIG. 1), of the first roll 4. Although the carrier web 1 cannot be overfed in the width direction X, the carrier web 1 in the present embodiment has a greater stretchability in the width direction X, perpendicular to the carrying direction Y of FIG. 1, than a stretchability in the carrying direction Y. Therefore, the carrier web 1 is unlikely to be damaged by the formation of the depressed portions 13 in the width direction X.

Downstream of the second roll 6 of FIG. 4, a countless number of granular particles 3 are dropped and dispensed from the dispenser device 5 onto the carrier web 1 with the depressed portions 13 and the protruding portions 14 formed thereon as shown in FIG. 6. That is, between the second roll 6 of FIG. 4 and the second introduction roller 72 for introducing the cover web 2, the granular particles 3 are dispensed from the dispenser device 5 onto the second surface 12, opposite to the first surface 11, of the carrier web 1 of FIG. 6 being carried. The dispensed granular particles 3 form a layer on the second surface 12.

The granular particles 3 may be dispensed intermittently for each absorbent body 200 (FIG. 1).

The layer of granular particles 3 may have a greater thickness in its center than in its opposite end portions in the axial direction of the first roll 4. Alternatively, the layer of granular particles 3 may have a smaller thickness along the periphery of one absorbent body 200 (FIG. 1) and have a greater thickness in the center of the layer or the vicinity of the center.

In FIG. 6, an air is drawn by the plurality of suction holes 40 formed in the first roll 4 through the air-permeable carrier web 1, thereby holding a large number of granular particles 3 on the depressed portions 13 of the carrier web 1. On the other hand, granular particles 3 on the protruding portions 14 would fall into the depressed portions 13 due to the airflow from the rotation of the first roll 4 or the suction of the air.

Note that in addition to the suction of the air, air discharge holes may be provided in the carrying surface 41 of the protruding portions 44 of the first roll 4 so as to discharge an air through discharge holes, thereby increasing the reliability that the granular particles 3 on the protruding portions 14 of the carrier web 1 are removed.

Through the placement step described above, the aggregate groups 30 made of a plurality (large number) of granular particles 3 are placed on the carrier web 1 separately in the placement areas D, which are the depressed portions 13 partitioned from one another by a predetermined pattern as shown in FIG. 2.

After the granular particles 3 are placed on the carrier web 1 in a predetermined pattern, the depressed portions 13 approach the second introduction roller 72 of FIG. 7. The protruding portions 14 (the second surface 12) of the carrier web 1, the openings of the depressed portions 13, and the granular particles 3 in the depressed portions 13 are covered by the cover web 2 introduced by the second introduction roller 72. Thus, the sandwich structure 20 is produced including the granular particles 3 sandwiched between the webs 1 and 2.

Then, as the sandwich structure 20 continues to be rotated by the carrying surface 41 to reach the ultrasonic horn 81 of FIG. 8, the carrier web 1 and the cover web 2, containing a thermoplastic resin, are ultrasonically welded together along the protruding portions 14 of the carrier web 1. Through the bonding step, the welded lines L, L of FIG. 3A are formed, thereby maintaining the predetermined pattern of the granular particles 3. After the webs 1 and 2 are welded together, the suction through the suction holes 40 (FIG. 6) and the discharge through the discharge holes may be stopped.

During the welding, another film, or the like, may be welded, in addition to the cover web 2 of FIG. 3B, but such a film may be bonded to the cover web 2 via an adhesive after the carrier web 1 and the cover web 2 are welded together.

Then, the sandwich structure 20 is cut into individual worn articles, i.e., into individual absorbent bodies 200 of FIG. 1.

While preferred embodiments have been described above with reference to the drawings, obvious variations and modifications will readily occur to those skilled in the art upon reading the present specification.

For example, the method for bonding the carrier web 1 and the cover web 2 with each other may be thermal welding such as heat seal, instead of ultrasonic welding.

Although the protruding portions formed on the top sheet 21 face the skin surface of the wearer when worn, with the back sheet 22 being flat, as shown in FIG. 3B, in the embodiment described above, the top sheet 21 may be flat while the back sheet 22 may be formed with protruding portions that are protruding away from the skin surface.

The present invention is not limited to cases where each placement area D includes therein only an aggregate of granular particles, and each placement area D may include therein a plurality of granular particles mixed with another granular material or a fiber material such as a pulp.

The plurality of depressed portions and protruding portions produced on the first continuous sheet do not have to have a uniform size and shape. For example, the length of some of the plurality of depressed portions in the longitudinal direction Y may be longer than the length of other depressed portions in the same direction Y. In such a case, for example, the length of some of a large number (plurality) of depressed portions of the second roll 6 in the longitudinal direction Y may be set to be longer.

The length of some of the plurality of depressed portions in the girth direction X, perpendicular to the longitudinal direction Y, may be longer than the length of other depressed portions. In such a case, for example, the length of some of a large number (plurality) of the second roll 6 in the girth direction X may be set to be longer.

Thus, such changes and modifications are deemed to fall within the scope of the present invention, which is defined by the appended claims.

INDUSTRIAL APPLICABILITY

The present invention is applicable to composite sheets in which granular particles are placed in a predetermined pattern, as well as absorbent bodies of disposable worn articles.

REFERENCE SIGNS LIST

1: Carrier web (an example of the first continuous sheet), 11: First surface, 12: Second surface, 13: Depressed portion, 14: Protruding portion 2: Cover web (an example of the second continuous sheet), 20: Sandwich structure, 21: Top sheet, 22: Cover sheet, 23: Core, 24: Back sheet 3: Granular particles, 30: Aggregate group, D: Placement area 4: First roll, 40: Suction hole (placement device), 41: Carrying surface, 43: Depressed portion, 44: Protruding portion 5: Dispenser device (placement device), 51: Oblong hole 6: Second roll, 63: Depressed portion, 64: Protruding portion 71: First introduction roller, 72: Second introduction roller 81: Ultrasonic horn 100: Worn article, 200: Absorbent body (an example of the composite sheet), 201: Front portion, 202: Back portion, 203: Crotch portion, 301: Front around-torso member, 302: Back around-torso member L: Welded line P1: First pitch, P2: Second pitch V1, V2: Circumferential velocity R: Circumferential direction, X: Girth direction (width direction), Y: Longitudinal direction (carrying direction)

The invention claimed is:

1. A method for manufacturing a composite sheet in which a plurality of granular particles are placed in a predetermined pattern between two sheets,
wherein the method uses a first roll having a plurality of first depressions and protrusions on a circumferential surface of the first roll, and a second roll having a plurality of second depressions and protrusions on a circumferential surface of the second roll, the second depressions and protrusions fitting with the first depressions and protrusions, the method comprising:
a step of carrying a first continuous sheet along a plurality of protruding portions of the second depressions and protrusions of the second roll so as to supply the first continuous sheet into between the first roll and the second roll;
a step of causing some of the second depressions and protrusions of the second roll and some of the first depressions and protrusions of the first roll to rotate while fitting with each other, with the first continuous sheet interposed therebetween, thereby forming a plurality of third depressions and protrusions on the first continuous sheet;
a placement step of placing the plurality of granular particles in depressed portions of the third depressions and protrusions;
a step of laying a second continuous sheet on the first continuous sheet so as to cover openings of the depressed portions of the third depressions and protrusions and the granular particles, thereby forming a sandwich structure; and
a bonding step of bonding the two sheets together along the protruding portions of the third depressions and protrusions,
wherein a circumferential velocity V2 of the second roll is greater than a circumferential velocity V1 of the first roll.

2. A method according to claim 1, wherein a pitch P2 of the second depressions and protrusions is greater than a pitch P1 of the first depressions and protrusions.

3. A method according to claim 2, wherein the first and second rolls are separately rotated without a rotational force being transferred between the first roll and the second roll via the first and second depressions and protrusions.

4. A method according to claim 3, wherein:
the first continuous sheet is air-permeable; and
in the placement step, the method further comprises a step of causing a suction force to act on the depressed portions of the first continuous sheet from the depressed portions of the first depressions and protrusions of the first roll, thereby holding the first continuous sheet on the circumferential surface of the first roll while holding the granular particles in the depressed portions of the third depressions and protrusions through the first continuous sheet.

5. A method according to claim 4, wherein the first continuous sheet has a greater stretchability in a width direction, perpendicular to a carrying direction, than a stretchability in the carrying direction.

6. A method according to claim 5, wherein:
each of the sheets contains a thermoplastic resin; and
the bonding step includes ultrasonically welding and thereby bonding the sheets with each other.

7. A device for manufacturing a composite sheet, in which a plurality of granular particles are placed in a predetermined pattern between two sheets,
a first roll having a plurality of first depressions and protrusions on a circumferential surface of the first roll;
a second roll having a plurality of second depressions and protrusions on a circumferential surface of the second roll, the second depressions and protrusions fitting with the first depressions and protrusions for carrying a first continuous sheet along a plurality of protruding portions of the second depressions and protrusions so as to supply the first continuous sheet into between the first roll and the second roll, wherein the first depressions and protrusions and the second depressions and protrusions rotate while fitting with each other with the first continuous sheet interposed therebetween, thereby forming a plurality of third depressions and protrusions on the first continuous sheet;
a placement device for placing a plurality of granular particles in depressed portions of the third depressions and protrusions;
an introduction roller for laying a second continuous sheet on the first continuous sheet so as to cover openings of the depressed portions of the third depressions and protrusions and the granular particles by the second continuous sheet, thereby forming a sandwich structure;
a bonding device for bonding the two sheets together along the protruding portions of the third depressions and protrusions; and
a control device for rotating the rolls so that a circumferential velocity V2 of the second roll is greater than a circumferential velocity V1 of the first roll.

8. A manufacturing device according to claim 7, wherein a pitch P2 of the second depressions and protrusions is greater than a pitch P1 of the first depressions and protrusions.

9. A manufacturing device according to claim 8, further comprising a driving device for separately rotating the first and second rolls without a rotational force being transferred between the first roll and the second roll via the first and second depressions and protrusions.

10. A manufacturing device according to claim 9, wherein:
the first continuous sheet is air-permeable; and
the manufacturing device further comprises air suction holes for causing a suction force to act on the depressed portions of the first continuous sheet from the depressed portions of the first depressions and protrusions of the first roll, thereby holding the first continuous sheet on the circumferential surface of the first roll while holding the granular particles in the depressed portions of the third depressions and protrusions through the first continuous sheet.

11. A manufacturing device according to claim 10, wherein:
each of the sheets contains a thermoplastic resin; and
the manufacturing device further comprises an ultrasonic horn for ultrasonically welding and thereby bonding the sheets with each other.

* * * * *